(12) United States Patent
Park et al.

(10) Patent No.: US 7,976,388 B2
(45) Date of Patent: Jul. 12, 2011

(54) ORAL CARE GAMING SYSTEM WITH ELECTRONIC GAME

(75) Inventors: Sung K. Park, Waban, MA (US); Douglas C. Dayton, Harvard, MA (US)

(73) Assignee: Umagination Labs, L.P., Newton, MA (US)

( * ) Notice: Subject to any disclaimer, the term of this patent is extended or adjusted under 35 U.S.C. 154(b) by 893 days.

(21) Appl. No.: 11/728,259

(22) Filed: Mar. 23, 2007

(65) Prior Publication Data
US 2007/0270221 A1    Nov. 22, 2007

Related U.S. Application Data

(60) Provisional application No. 60/785,920, filed on Mar. 24, 2006, provisional application No. 60/851,373, filed on Oct. 13, 2006.

(51) Int. Cl.
G06F 17/00 (2006.01)
G06F 19/00 (2006.01)

(52) U.S. Cl. .................. 463/37; 463/1; 463/36; 463/42; 15/105

(58) Field of Classification Search ................ 463/1, 36, 463/37, 42; 434/263; 15/105, 167.1
See application file for complete search history.

(56) References Cited

U.S. PATENT DOCUMENTS

| | | | | |
|---|---|---|---|---|
| 4,253,212 A * | 3/1981 | Fujita | ........................... | 15/167.1 |
| 4,450,599 A * | 5/1984 | Scheller et al. | ................. | 15/22.1 |
| 5,864,288 A * | 1/1999 | Hogan | ....................... | 340/568.1 |
| 6,199,239 B1 * | 3/2001 | Dickerson | ....................... | 15/105 |
| 6,389,633 B1 * | 5/2002 | Rosen | ............................. | 15/105 |
| 6,536,068 B1 * | 3/2003 | Yang et al. | ....................... | 15/105 |
| 6,609,977 B1 * | 8/2003 | Shimizu et al. | .................. | 463/36 |
| 6,611,780 B2 * | 8/2003 | Lundell et al. | ................. | 702/122 |
| 6,754,928 B1 * | 6/2004 | Rosen | ............................. | 15/105 |
| 6,786,732 B2 * | 9/2004 | Savill et al. | .................... | 434/263 |

(Continued)

FOREIGN PATENT DOCUMENTS

FR    2544602 A1 * 10/1984

(Continued)

OTHER PUBLICATIONS

"Int'l Search Report for PCT/US07/007501", (Aug. 3, 2007).

(Continued)

*Primary Examiner* — Milap Shah
(74) *Attorney, Agent, or Firm* — Strategic Patents, P.C.

(57) ABSTRACT

An oral care gaming system and methods are provided for promoting and rewarding proper oral care techniques and behaviors and for controlling an electronic and/or video game. The system and methods enable a user to play an electronic and/or video game while performing certain oral care activities. The efficacy of a user's oral care techniques enables the user to improve their game play and to achieve the goals of the game. The system includes an oral care tool configured as a game enabler/controller and a base unit configured as an electronic gaming apparatus. Using the oral care tool, a user performs oral care and interacts with an electronic and/or video game the base unit implements and runs. The base unit includes a video display that displays video outputs of an electronic and/or video game. The oral care tool is actuated to enable an electronic and/or video game, and includes sensors for detecting characteristics of a user's oral care techniques and behaviors that serve as inputs to an electronic and/or video game.

20 Claims, 7 Drawing Sheets

U.S. PATENT DOCUMENTS

| | | | |
|---|---|---|---|
| 6,850,167 B2 * | 2/2005 | Rosen | 340/689 |
| 7,001,270 B2 * | 2/2006 | Taub | 463/1 |
| 7,013,522 B2 * | 3/2006 | Kumagai | 15/105 |
| 7,748,069 B2 * | 7/2010 | Dawley | 15/22.1 |
| 2002/0115482 A1 * | 8/2002 | Taub | 463/1 |
| 2003/0017874 A1 | 1/2003 | Jianfei et al. | 463/46 |
| 2004/0019990 A1 * | 2/2004 | Farrell et al. | 15/105 |
| 2005/0091768 A1 | 5/2005 | Davics et al. | 15/22.1 |
| 2005/0119050 A1 * | 6/2005 | Suzuki | 463/36 |
| 2005/0245839 A1 * | 11/2005 | Stivoric et al. | 600/549 |
| 2006/0040246 A1 * | 2/2006 | Ding et al. | 434/263 |
| 2006/0061323 A1 * | 3/2006 | Cheng et al. | 320/108 |
| 2006/0068911 A1 * | 3/2006 | Pirich et al. | 463/40 |
| 2007/0074359 A1 * | 4/2007 | O'Lynn | 15/105 |
| 2007/0136964 A1 * | 6/2007 | Dawley | 15/22.1 |
| 2007/0270221 A1 * | 11/2007 | Park et al. | 463/37 |
| 2008/0102953 A1 * | 5/2008 | Schultz | 463/37 |
| 2008/0141476 A1 * | 6/2008 | Gatzemeyer et al. | 15/105 |
| 2009/0092955 A1 * | 4/2009 | Hwang | 434/263 |

FOREIGN PATENT DOCUMENTS

WO     WO 00/78421 A1     12/2000

OTHER PUBLICATIONS

ISA, , "International Search Report and Written Opinion", For US Patent Application No. PCT/US07/007501, mailed on Aug. 3, 2007 Jul. 24, 2007.

* cited by examiner

ORAL CARE GAMING SYSTEM WITH ELECTRONIC GAME

CLAIM OF PRIORITY TO PRIOR APPLICATION

This patent application claims priority to U.S. provisional patent application No. 60/785,920, filed Mar. 24, 2006, and to U.S. provisional patent application Ser. No. 60/851,373, filed Oct. 13, 2006, the disclosures of which are incorporated herein in their entireties by reference.

TECHNICAL FIELD OF THE INVENTION

The invention relates to an oral care gaming system and methods for promoting and rewarding proper oral care techniques and behaviors and for controlling an electronic and/or video game. More particularly, the system and methods enable a user to play an electronic and/or video game while performing oral care activities, wherein the efficacy of a user's oral care techniques enhance the user's game play.

BACKGROUND OF THE INVENTION

Oral care, such as teeth brushing, flossing and/or gum stimulation, is recognized as an important part of overall personal health and hygiene. Many oral care products and practices may be disliked by people, including children, because such products and practices are uncomfortable and/or boring. People therefore tend to inadequately, inconsistently and/or superficially care for their teeth and/or gums. In addition, people, including children, often do not brush their teeth for a sufficient amount of time to adequately clean teeth and/or do not properly or consistently floss their teeth or otherwise care for their gums.

Dentists recommend for proper oral care and optimal oral hygiene people brush their teeth for at least two minutes after every meal to adequately clean teeth. In addition, dentists recommend flossing teeth after each brushing. Children can become impatient and/or bored while brushing their teeth and cease brushing before achieving the recommended two minute brushing, or brush superficially or inconsistently. As a result, children may not practice effective oral care techniques and may not achieve adequate or optimal oral care and hygiene.

SUMMARY OF THE INVENTION

The invention provides a system and method that creates a more entertaining environment for oral care that enables an electronic and/or video game wherein a user can perform well at the game and/or achieve the goals of the game by practicing proper oral care techniques. For instance, in the context of tooth brushing, the system and method encourages a user to brush their teeth using the system, e.g., for a recommended period of time, and to brush their teeth with suggested techniques in order the user may play an electronic and/or video game and work towards achieving one or more goals of the game. The user's efficacy of oral care techniques and behaviors is rewarded with enhanced or improved game performance thereby encouraging and reinforcing such techniques and behaviors. The system and method thereby motivate users, especially children, to brush their teeth regularly and for a recommended period of time. The invention however is not limited to the context of tooth brushing, and those of ordinary skill in the art will recognize the system and method of the invention can be configured and used for a number of different oral care tasks, including, but not limited to, flossing teeth, massaging gums and water-jetting teeth.

In an aspect, the invention provides an oral care gaming system comprising a first oral care tool configured for maintenance or treatment of a condition in the mouth or organs therein. The oral care tool comprises one or more sensors for detecting temperatures of a user's mouth and communication means for communicating with another component operatively coupled with the oral care gaming system. The oral care gaming system further comprises an electronic gaming apparatus operatively coupled with the oral care tool. The electronic gaming apparatus comprises communication means for communicating with the oral care tool and a processor configured to control at least one electronic game. The at least one electronic game provides an output perceivable by a user of the oral care tool. The output of the electronic game is responsive to inputs received from the one or more sensors.

Implementations of the invention may include one or more of the following features. The communication means of the oral care tool and the communication means of the electronic gaming system includes one or more electrical conductors that connect the oral care tool to the electronic gaming apparatus. Alternatively, or additionally, the at least one of the communication means of the oral care tool and the communication means of the electronic gaming system includes a wireless transmission system configured to establish a wireless communication link between the oral care tool and the electronic gaming apparatus. The electronic gaming apparatus further includes memory operatively coupled with the processor and storing at least one set of instructions for implementing at least one regimen of oral care maintenance or treatment. The output of the electronic game is implemented in accordance with the at least one set of instructions.

Implementations of the invention may also include one or more of the following features. The electronic gaming apparatus further includes at least one external communication port for interconnection with at least one input device disposed remotely relative to the electronic gaming apparatus or the first oral care tool. The at least one input device includes at least one of a computer, a computing device and an internet communication device configured to provide inputs to the processor. The electronic gaming apparatus further includes means to establish a wireless communications link between the electronic gaming apparatus and at least one input device disposed remotely relative to the electronic gaming apparatus or the first oral care tool.

Implementations of the invention may further include one or more of the following features. A timer to determine a duration of use of the first oral care tool for a given oral care session. The output of the electronic game ceases upon the processor receiving inputs from the one or more temperature sensors detecting a cessation of use of the first oral care tool before the expiration of the given oral care session. The output of the electronic game resumes upon the processor receiving inputs from the one or more temperature sensors detecting a resumption of use of the first oral care tool before the expiration of a given interval of time.

Implementations of the invention may include one or more of the following. The another component operatively coupled with the oral care gaming system includes at least the electronic gaming apparatus. The system further comprises at least a second oral care tool configured for maintenance or treatment of a condition in the mouth or organs therein. The second oral care tool comprises one or more sensors for detecting temperatures of a user's mouth, and communication means for communicating with the another component operatively coupled with the oral care gaming system. The another component includes at least the electronic gaming apparatus. The inputs received from the one or more sensors of the first and the second oral care tools are coupled onto the output of the same electronic game. Alternatively, or additionally, the inputs received from the one or more sensors of the first oral care tool are coupled onto the output of a first electronic game and inputs received the one or more sensors of the second oral care tool are coupled onto the output of a second electronic game.

Implementations of the invention may also include one or more of the following features. The oral care tool includes a device selected from the group consisting of a tooth brush, a flossing device, a gum stimulating instrument, a water-jet device, an implement configured as any combination thereof, and any combination thereof. The first and the second oral care tools each include a device selected from the group consisting of a tooth brush, a flossing device, a gum stimulating instrument, a water-jet device, an implement configured as any combination thereof, and any combination thereof. Alternatively, or additionally, the first oral care tool further comprises one or more sensors for detecting pressures which the first oral care tool applies to at least one of a user's mouth and a user's teeth, and wherein the output of the electronic game being responsive to one or more inputs received from the one or more pressure sensors. Alternatively, or additionally, the first oral care tool further comprises one or more sensors for detecting at least one of movement, direction and acceleration of the first oral care tool within a user's mouth and along a user's teeth, and wherein the output of the electronic game is responsive to inputs received from the movement, direction or acceleration sensors. The electronic gaming apparatus further comprises a video display for displaying the output of the electronic game.

In another aspect, the invention provides a method of promoting proper oral care, the method comprising sensing temperatures of a user's mouth indicative of the use of an oral care tool within the user's mouth, and communicating outputs from one or more sensors sensing temperatures as inputs to a processor configured to control an electronic game, the electronic game providing an output perceivable by a user of the oral care tool. The method further comprises providing game output that is responsive to the inputs received from the one or more temperature sensors.

Implementations of the method of the invention may include one or more of the following features. The method further comprises ceasing game output in response to a cessation of the inputs received from the one or more temperature sensors, and comprises resuming game output in response to a resumption of the inputs received from the one or more temperature sensors within an interval of time. Wherein providing game output includes continuing game output for a duration of an oral care session in response to receiving the inputs from the one or more temperature sensors. The duration of an oral care session proceeds in accordance with at least one set of instructions.

In an further aspect, the invention provides a method of interacting with an oral care game. The method comprises selecting and attaching an oral care tool head to a handle to complete an oral care tool, activating an electronic gaming apparatus, selecting an electronic game, and sensing one or more physical parameters indicative of the use of the oral care tool. The method further comprises transmitting physical parameter data to a processor of the electronic gaming apparatus, receiving the physical parameter data at the processor, utilizing the physical parameter data to create and to display the output of the electronic game, and alerting a user of the oral care tool of the expiration of an oral care session.

Implementations of such method of the invention may include one or more of the following features. The sensing one or more physical parameters includes sensing temperatures of a user's mouth in which the oral care tool resides during oral care activity. The method further comprises identifying a user of the oral care tool by identifying one or more identification or encoded inputs elicited from the oral care tool head. Additionally, or alternatively, the method comprises identifying an oral care activity to be performed with the oral care tool by identifying one or more identification or enclosed inputs elicited from the oral care tool head.

Various embodiments of the invention provide one or more of the following capabilities. An oral care gaming system can be configured with an oral care tool constructed and arranged for maintenance or treatment of the mouth, gums and/or teeth and for serving as a game enabler/controller. The oral care tool includes one or more input switches and one or more sensors integrated with the tool to enable electronic and/or video game entertainment to a user of the system, while the user is employing the tool to perform oral care functions and activities. The oral care tool can employ user-provided inputs and sensor outputs to play and to control an electronic and/or video game. The system can provide a user with oral care feedback to motivate and to reinforce the user to perform and to improve oral care efficacy. The system can provide a user with feedback regarding their oral care efficacy by enhancing or improving the user's game performance, game scoring, game progress and/or achieving one or more goals of an electronic and/or video game the user interacts with.

The oral care tool communicates with a base unit configured as an electronic gaming apparatus either through wired or wireless connection. The base unit comprises a microcomputer system, a power supply and a timer or real-time clock, each of which provide outputs to a video display that provides video images of an electronic and/or video game and to one or more speakers that provide audio feedback of the game. The microcomputer system includes an addressable memory or interchangeable memory that incorporates electronic computer software for enabling, implementing, initiating, playing and/or displaying one or more electronic and/or video games. The base unit includes one or more external communication ports to communicate with and to receive inputs from at least a second oral care tool that is disposed remote from the oral care tool and includes one or more inputs for providing game inputs and game control commands to the base unit. The one or more external communication ports also permit interconnection of the base unit with one or more other computing devices, computers and/or the internet, and/or provide a docking station for external memory cartridges, and/or provide interconnections for downloading external software to the base unit.

The microcomputer system can be configured to analyze and to produce oral care efficacy ratings that can be used to modify, e.g., enhance or improve game scoring, game performance and achieving game goals. The efficacy ratings are produced by the microcomputer system using the outputs of one or more sensors residing in the oral care tool that detect, sense and/or measure characteristics of oral care activities while a user is performing such activities with the oral care tool.

These and other aspects and embodiments of the invention, along with the invention itself, will be more fully understood after a review of the figures, the detailed description and the claims, as provided below.

DETAILED DESCRIPTION OF THE INVENTION

Figure 1:
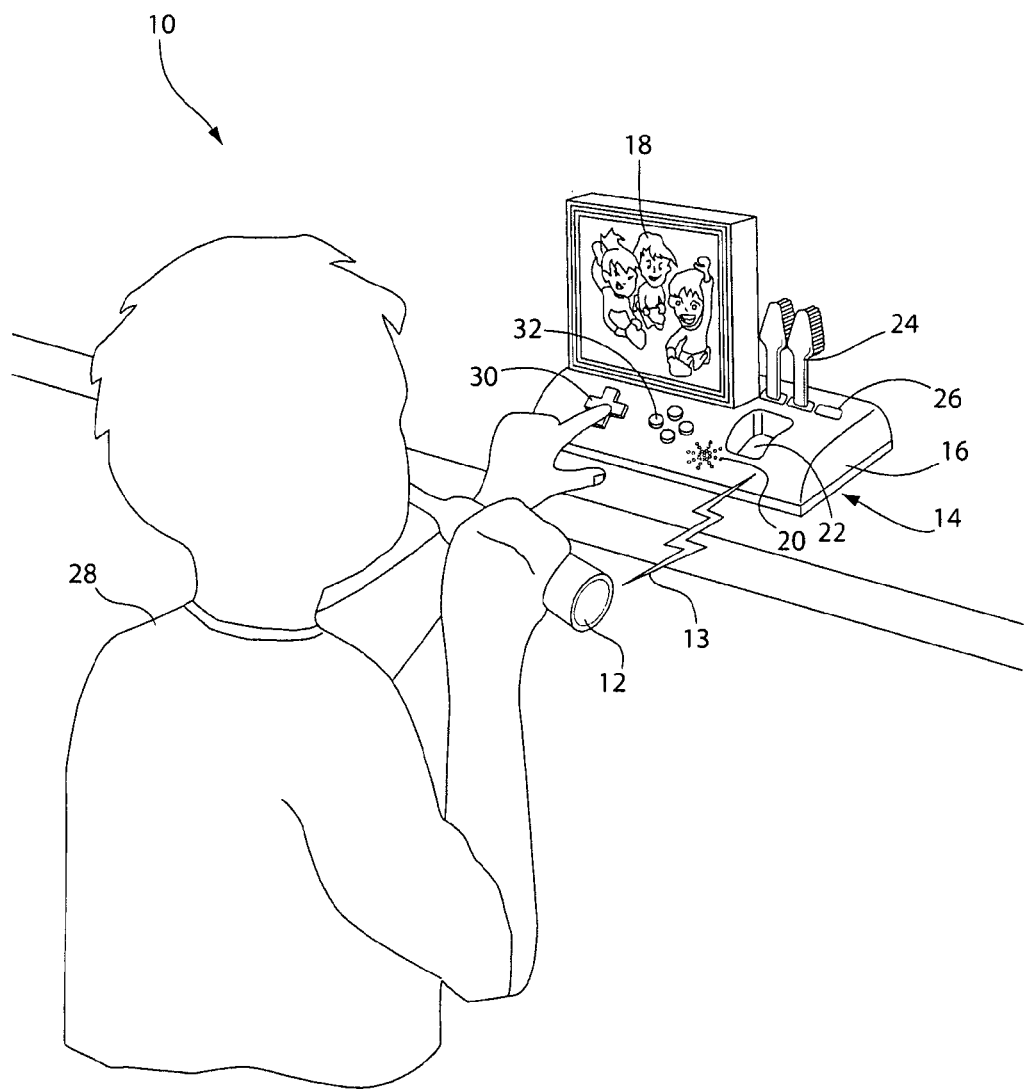
FIG. 1 is a schematic diagram of one embodiment of the oral care gaming system.

Embodiments of the invention provide an oral care gaming system for implementing one or more electronic and/or video games and for enabling a user of the system to control the play of an electronic and/or video game by performing oral care activities. The system enables one or more electronic and/or video games wherein achieving goals of a game and enhancing game performance are possible by a user's oral care techniques and behaviors. The system provides a user with feedback regarding the efficacy of their techniques and behaviors during oral care sessions through enhanced or improved game performances and achievement of game goals. By permitting a user to play an electronic and/or video game during oral care, the system entertains the user and motivates and reinforces the user to strive to achieve proper oral care techniques and ultimately optimal oral care.

Exemplary embodiments of the oral care gaming system and method comprise an oral care tool for performing various oral care functions and for serving as a game enabler/controller. The system further comprises a base unit operatively coupled to the oral care tool which serves as an electronic gaming apparatus disposed remotely from the oral care tool and configured to run and to display one or more electronic and/or video games. Using the oral care tool for oral care functions, a user of the system engages and interacts with an electronic and/or video game the base unit runs. The oral care tool comprises one or more sensors for detecting a user's orientations of the oral care tool and for sensing, detecting and/or measuring the user's oral care techniques and behaviors. When activated, the sensors communicate with the base unit and therein activate the base unit to implement, initiate, play and/or display a game. More particularly, the sensors provide sensor feedback outputs as inputs into a microprocessor and/or a microcomputer system contained in the oral care tool and/or the base unit, respectively. The microprocessor and/or microcomputer system is programmed to analyze the sensor feedback inputs and to compute one or more ratings of the efficacy of the user's oral care techniques and behaviors. The system is programmed to translate a user's efficacy ratings into enhanced or improved game performances, game scoring and/or achieving one or more game goals.

The oral care tool further includes means for hard wired and/or wireless communication with the base unit, and can further include one or more manual input switches to generate signals as game inputs and game control commands for transmission to the base unit. The base unit includes hard wired and/or wireless communication means for communication with the oral care tool. The base unit further includes a video display for providing video images of an electronic and/or video game and one or more speakers for producing audio feedback of an electronic and/or video game. The base unit includes a microcomputer system including one or more power supplies, a timer or a real-time clock, and addressable memory or interchangeable memory that incorporates electronic computer software for implementing and for running one or more electronic and/or video games. The base unit can also include one or more manual input switches for selecting a mode of operation of the system and for generating game inputs and game control commands. The base unit can further include one or more external communication ports configured to permit interconnection of the base unit with one or more other components that can be incorporated with the system including, but not limited to, one or more other input devices, e.g., one or more computers, internet communication devices and/or computing devices, remotely disposed relative to the oral care tool and including one or more inputs for generating game inputs and game control commands. Alternatively, the base unit can be configured and programmed to provide wireless communication with such other input devices. The one or more external communication ports can also be configured to permit interconnection with the internet, and/or to provide a docketing station for receiving external memory cartridges, and/or to provide the ability to download external software. In addition, the base unit can be programmed to communicate with at least a second oral care tool to receive game inputs and control commands and sensor feedback inputs from the second oral tool to thereby configure the system and method as a multi-user or multi-player system.

Referring to FIG. 1, in an aspect, the invention provides an oral care gaming system 10 including an oral care tool 12 and a base unit 14. The oral care tool 12 is constructed and arranged for maintenance or treatment of the mouth, gums and/or teeth and is further designed and configured as a game enabler/controller to communicate with the base unit 14 and to interact with an electronic and/or video game of the base unit 14. The oral care tool 12 can include, but is not limited to, a toothbrush, a flossing device, a gum stimulating instrument, a water-jet device or an implement configured as any combination thereof, and is configured to perform one or more oral care functions or activities, e.g., brushing, flossing, massaging or water-jet motions. For purposes of disclosure of the invention, the oral care tool 12 is described below with reference to a toothbrush 12 and within the context of tooth brushing. Those of ordinary skill in the art will recognize that the invention is not limited to the toothbrush 12 illustrated and described and envisions the oral care tool 12 can include other oral care devices and instruments, such as, but not limited to, those mentioned above, for performing any of a variety of oral care functions.

The base unit 14 is designed and configured as an electronic gaming apparatus including, as will be described below, electronics for interacting and communicating with the oral care tool 12 and for enabling one or more electronic and/or video games. The base unit 14 includes a housing 16 and a video display 18, e.g., a video monitor or an LCD screen, connected to the housing 16 and configured to display video images of one or more electronic and/or video games the base unit 14 implements, initiates, plays and/or displays. The base unit 14 further includes one or more speakers 20 to produce audio feedback generated during implementation, initiation and play of one or more games.

The housing 16 can further define a receptacle 22 configured to receive and to thereby mount the tool 12 to the base unit 12 when it is not in use. As will be described below, the oral care tool 12 can be configured to removably receive a multiple of replaceable oral care tool heads 24, e.g., toothbrush heads, such that the tool 12 can be used by a multiple of users. The oral care tool 12 can also be configured to removably receive a multiple of different and replaceable oral care tool heads 24 wherein each head 24 is configured to perform a specific oral care function, e.g., tooth brushing, flossing, gum massaging or water-jetting teeth.

In one embodiment of the system 10 configured for multiple users, the housing 16 can define a multiple of tool head receptacles 26, each configured to receive and to thereby mount to the housing 16 a tool head 24 for each individual user of the system 10. In another embodiment of the system 10 configured for performing multiple oral care functions, the housing 16 can define a multiple of receptacles 26, each configured to receive and to thereby mount to the housing 16 one or more different tool heads 24, such as a tooth brush head, a flossing device head, a gum stimulating tip and/or a water-jetting head, for each oral care function the system 10 is configured to perform.

The base unit 14 can further include one or more manual input switches 30 and 32 operatively coupled with electronics of the base unit 14, as will be described below. The switches 30 and 32 are disposed along the housing 16 to permit a user 28 to access the one or more switches 30 and 32 to provide game inputs and game control commands to the base unit 14, to select operating modes of the base unit 14, and to play and/or to control an electronic and/or video games of the base unit 14.

As shown in FIG. 1, in a preferred embodiment of the system 10, the oral care tool 12 and the base unit 14 are operatively coupled for wireless communication 13. A user 28 communicates with the base unit 14 by manually holding and manipulating the tool 12 to perform oral care functions, and by actuating one or more manual input switches (not shown) along the tool 12 and/or by actuating the one or more manual input switches 30 and 32 of the base unit 14, to select an operating mode of the system 10 and to provide game inputs and game control commands to the base unit 12 to thereby activate the base unit 14 to implement, initiate, play and/or display an electronic and/or video game.

Figure 2:
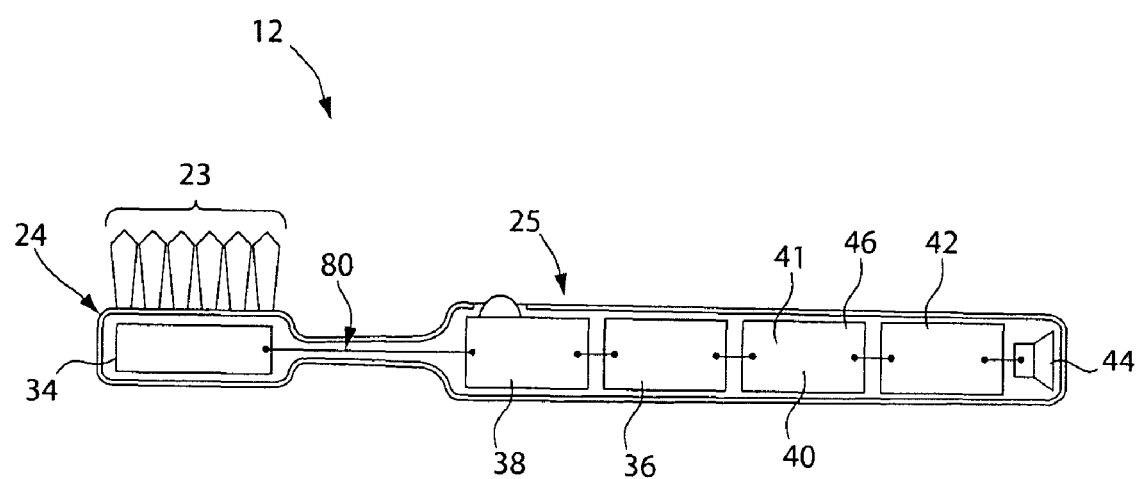
FIG. 2 is a schematic diagram of the oral care tool shown in FIG. 1.

Referring to FIG. 2, and with further reference to FIG. 1, a schematic diagram illustrates an exemplary oral care tool 12 including a tool head 24 and a handle 25. In a preferred embodiment of the invention, the tool head 24 is a tooth brush head 24 including a plurality of bristles 23. The tool 12 further includes one or more sensors 34 and 36, one or more manual input switches 38, a printed circuit board (PCB) 40 and associated electronics, an internal communication module 41, one or more power sources 42 and one or more speakers 44.

The tool head 24 is configured to house within its interior one or more sensors 34, and the handle 25 is configured to house within its interior one or more sensors 36. The sensors 34 and 36 can include various sensors for detecting, sensing, and/or measuring one or more physical parameters of oral care activities as variables, characteristics and behaviors of oral care that are being performed with the oral care tool 12. When one or more of the sensors 34 and 36 are activated during oral care activities, the communication module 41 wirelessly communicates sensor outputs to the base unit 14 to activate the base unit 14 to implement, initiate, play and/or display an electronic and/or video game. A user of the system 10 can thereby interact through their performance of oral care functions, as detected by the one or more sensors 34 and 36, with the game content the base unit 14 runs.

The sensors 34 of the tool head 24 can include one or more pressure transducers configured to detect pressure the brush bristles 23 and/or the brush head 24 apply to a user's mouth and/or teeth, and/or one or more accelerometers configured to sense movements or brushing accelerations of the brush head 24, and/or one or more temperature or thermal sensors configured to measure temperatures of a user's mouth or oral cavity during brushing. As will be described below, the outputs of the temperature or thermal sensors 34 help to ensure that brushing with the brush head 24 is occurring in a user's mouth rather than the user simply simulating brushing to play and to score a game.

The one or more sensors 36 disposed within the handle 25 interior can include one or more strain gauges, load cells, force transducers, accelerometers, gravity sector sensors, gyroscopes and/or other motion or load sensing devices or sensors.

The sensors 34 and 36 are activated by oral care activities and generate sensor outputs to implement, initiate, play and control an electronic and/or video game of the base unit 14. For instance, in the preferred embodiment wherein the oral care tool 12 is a toothbrush, while a user brushes their teeth with the tool 12, certain brushing techniques and behaviors, such as appropriate toothbrush pressure, brushing motion with respect to uniformity and direction, tooth surfaces brushed, e.g., top, bottom, inside, outside surfaces, and brushing duration, e.g., for a predetermined period of time, are detected or measured by one or more of the sensors 34 and 36. The sensor 34 and 36 outputs are analyzed by a microprocessor 46 of the oral care tool 12 and/or a microcomputer system 50 of the base unit 14, as will be described below, to produce efficacy ratings and to translate the sensor outputs, representing a user's tooth brushing techniques and behaviors, into game control, game scoring, and improved or enhanced play of an electronic and/or video game. The potentials for achieving enhanced or improved game performance, higher game scoring and one or more game goals are thereby tied to a user's actual brushing and to their tooth brushing techniques and behaviors.

In the preferred embodiment of the invention, the brush head 24 contains within its interior one or more temperature or thermal sensors 34 for detecting temperatures of a user's 28 mouth while the user 28 brushes their teeth with the tool 12. The temperature and thermal sensor 34 outputs enable a user 28 to play a game of the base unit 14 using the tool 12 and, as mentioned, ensure that the user 28 plays the game by brushing their teeth with the tool 12 in their mouth as opposed to the user 28 simulating tooth brushing in order to play the game. In addition, the temperature or thermal sensor 34 outputs can be used to measure the duration of tooth brushing, e.g., for a predetermined period of time the base unit 14 is preset and/or programmed to track and to control. If the temperature or thermal sensor 34 outputs indicate a cessation of tooth brushing with the tool 12 in a user's mouth before the expiration of a period of time, the base unit 14 can be programmed to respond to the brushing cessation in a number of different ways, as describe below, including, for instance, suspending game play if the interval of brushing cessation exceeds a preset or programmed limit or time interval.

In addition, the microprocessor 46 of the oral care tool 12 and/or the microcomputer system 50 of the base unit 14 can analyze sensor outputs, such as, sensor outputs produced from one or more pressure transducers 34 and 36, representing detected pressures the brush bristles 23 and the brush head 24 apply to a user's teeth, and/or sensor outputs from one or more accelerometers 34 and 36, representing the brush head 24 motions/movements with respect to direction, uniformity and/or accelerations. As will be described below, the microprocessor 46 and/or the microcomputer system 50 can analyze sensor outputs of the temperature or thermal sensors 34, the pressure transducers 34 and 36 and/or the accelerometers 34 and 36, individually, as separate variables or parameters, and/or in conjunction with one another or with other sensor outputs received from other sensors 34 and 36 to help to produce efficacy ratings of a user's tooth brushing techniques and behaviors. For instance, the outputs of the temperature or thermal sensors 34 can be analyzed in conjunction with the outputs of the pressure transducers 36 to provide efficacy ratings with respect to the duration of a user's tooth brushing and uniformity of the user's brushing technique during a brushing session.

The brush head 24 of the oral tool 12 may be non-powered or powered, and either powered or non-powered brush heads 24 can be used with any of the above-noted sensors 34 and 36. In the preferred embodiment, the brush head 24 is powered by the one or more power sources 42. The power sources 42 reside within the handle 25 and include self-contained power sources 42 such as, but not limited to, batteries, fuel cells, photovoltaic cells, chemical power cells or any other self-contained electrical energy power source.

In addition, the oral tool 12 is configured to removably receive multiple brush heads 24. Each brush head 24 is configured for removable attachment to the tool 12 to thereby configure the system 10 as a multi-user or multi-player system 10. As will be described below, in the preferred embodiment, each brush head 24 is programmed and/or is encoded 80 to identify a specific user 28 associated with the brush head 24 such that the base unit 14, e.g., a microcomputer 50 of the base unit 14, identifies the brush head 24 to thereby identify the specific user 28 of the system 10 when the brush head 24 is attached to the oral care tool 12. As will be described below with reference to FIG. 5, the programmed and/or encoded 80 brush heads 24 help to configure the system 10 as a multi-user or multi-player system 10.

In the preferred embodiment, the tool 12 further includes the one or more manual input switches 38 disposed along the handle 25 such that each switch 38 is actuated from an area external to the handle 25. Each switch 38 is further disposed and is configured to operatively couple with electronics of the printed circuit board (PCB) 40 contained within the handle 25 interior. Actuation of the one or more switches 38 produces output signals transmitted to and received by the PCB 40 as game inputs and game control commands which the communication module 41 communicates wirelessly to the base unit 14. In the preferred embodiment, actuation of the one or more switches 30 and 32 located at the base unit 14 and/or actuation of the one or more switches 38 disposed along the tool handle 25 provide game input and game control command signals to the base unit 14 for enabling initiation, play and control of an electronic and/or video game.

In addition, the one or more switches 38 of the oral care tool 12 can, upon actuation, implement and/or activate certain operating modes of the system 10, including, but not limited to, a video play mode, a display mode and/or a non-video mode. For instance, the video play mode, when activated, enables a user to play an electronic and/or video game using the oral care tool 12. In the display mode, the system 10 displays at the video display 18, for instance, a user's game data, e.g., game status, game results, game standings, achievement of game goals, and other information related to a user's game performance. In addition, the system 10 displays at the video display 18 a user's oral care data including, for instance, efficacy ratings and prescribed oral care regimens. Such game data and oral care data can be recorded and stored by the system 10 and thereafter displayed by the system 10 at the video display 18 as current, cumulative and/or historical compilations, files and records. When activated, the non-video mode of the system 10 permits a user to use the oral care tool 12 for oral care functions without playing an electronic and/or video game.

The one or more switches 38 located along the handle 25 can define any of a variety of configurations and structures including, but not limited to, force-sensitive touch pads, small joysticks, discrete buttons, toggle switches, slider switches, any combination thereof, and other input configurations and structures suitable for enabling input and command control signals.

As shown in FIG. 2, in the preferred embodiment, the PCB 40 is operatively coupled to the one or more switches 36 of the tool 12 and is also operatively coupled to the one or more power sources 42 disposed within the handle 25 interior. In the preferred embodiment, the PCB 40 includes the microprocessor 46 configured for, as mentioned, analyzing sensor output signals the microprocessor 46 receives as inputs from the one or more sensors 34 and 36, and for analyzing and/or receiving game inputs and game control commands it receives from the one or more switches 38 of the tool 12.

In addition, the PCB 40 is operatively coupled to the internal communication module 41 configured for creating a wireless link 13 between the oral care tool 12 and the base unit 14. The communication module 41 enables wireless communication 13 of output signals that the microprocessor 46 provides as a result of analyzing sensor feedback and analyzing and/or receiving game inputs and game control commands from the switches 38. The communication module 41 comprises one or more transmitting devices configured and programmed to establish the wireless link 13 for communicating any of the outputs of the microprocessor 46, the sensors 34 and 36 and the one or more manual input switches 38 of the oral care tool 12 to the base unit 14. The transmitting devices of the communication module 41 can include, but are not limited to, infrared or laser LED devices, 802.11 interfaces, Bluetooth® connections, other infrared (RF) transmission devices and systems, and any combination thereof.

With further reference to FIG. 2, the tool 12 includes one or more speakers 44 configured to produce audio output from audio feedback the base unit 14 generates as a result of implementing, initiating and/or playing an electronic and/or video game. In the preferred embodiment, the one or more speakers 44 are contained within the interior of the handle 25 and are operatively connected to the PCB 40 and the communication module 41 to receive audio feedback from the base unit 14.

Figure 3:
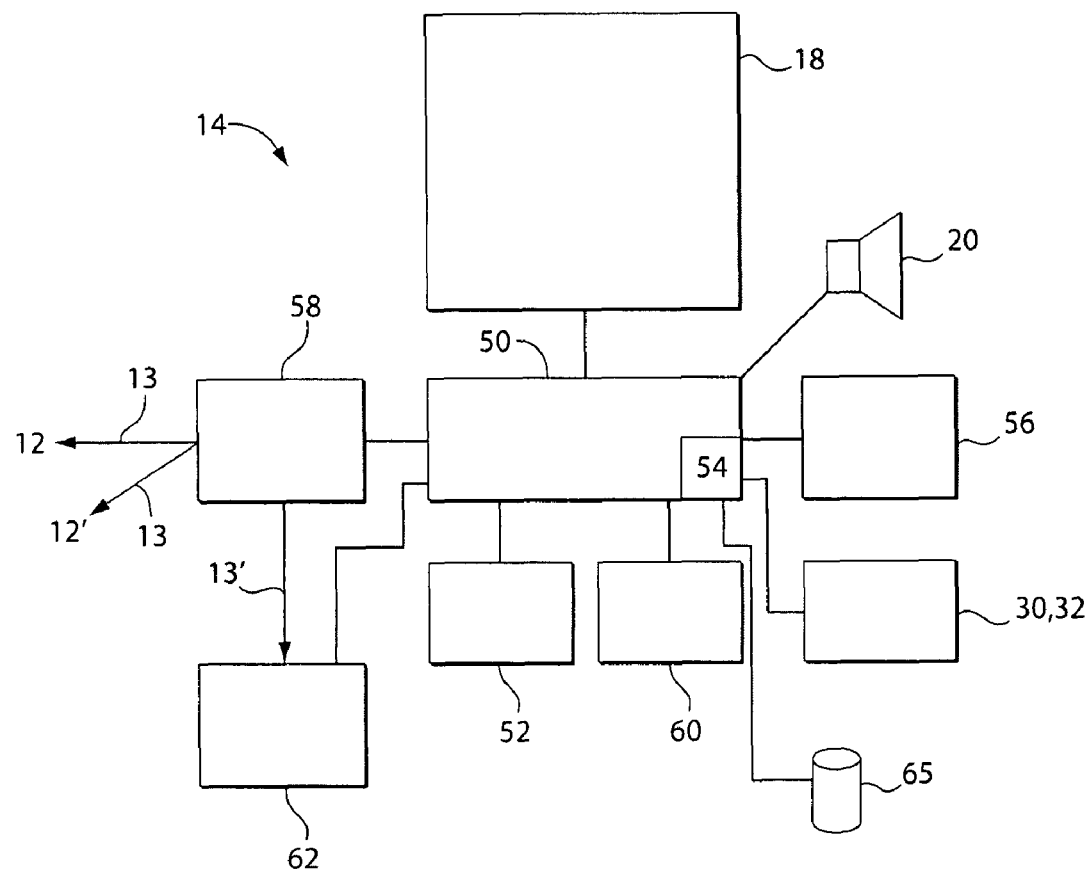
FIG. 3 is a schematic diagram of the embodiment of the base unit shown in FIG. 1.

Referring to FIG. 3, and with further reference to FIGS. 1 and 2, an exemplary schematic system design of the base unit 14 is illustrated. In the preferred embodiment, the base unit 14 is configured and programmed to serve as an electronic gaming apparatus comprising the microcomputer system 50, the video display 18, the one or more speakers 20, a power supply 52, a timer or real-time clock 54, addressable memory or interchangeable memory 56, the one or more manual input switches 30 and 32, an internal communication module 58, and one or more external communication ports 60.

The microcomputer system 50 is operatively coupled to the power supply 52, the video display 18, e.g., a video monitor or an LCD screen, the one or more manual input switches 30 and 32, the one or more speakers 20 and the timer or real-time clock 54. The one or more manual input switches 30 and 32 provide input signals to the microcomputer system 50 to implement and/or to activate certain operating modes of the system 10, including, but not limited to, a video play mode, a display mode and/or a non-video mode, as described above. In addition, the input signals from the manual input switches 30 and 32 implement, initiate, play and/or display an electronic and/or video game residing in the base unit 14.

Video outputs of the microcomputer system 50 and of the timer or real-time clock 54 are produced to the video display 18, which is configured to display video outputs to provide video images of an' electronic and/or video game the base unit 14 runs, and to provide video images of the base unit's 14 interactions with the oral care tool 12. In addition, audio feedback outputs of the microcomputer system 50 are produced to the one or more speakers 20, which are configured to play audio feedback outputs to produce sound of an electronic and/or video game the base unit 14 runs.

In addition, the microcomputer system 50 is operatively coupled to the addressable memory or interchangeable memory 56 which incorporates electronic computer software for one or more electronic and/or video games to configure and to program the base unit 14

Further, the microcomputer system 50 is operatively coupled to the internal communication module 58. In the preferred embodiment, the internal communication module 58 is configured and is programmed to create the wireless communication link 13 between the base unit 14 and the oral care tool 12. The communication module 58 comprises one or more transmitting devices to establish the wireless link 13 between the base unit 14 and the oral care tool 12, including, but not limited to, infrared or laser LED devices, 802.11 interfaces, Bluetooth® connections, other infrared (RF) transmission devices and system, and any combination thereof.

The microcomputer system 50 is also operatively coupled to the one or more external communication ports 60. The one or more external communication ports 60 can include ports configured to permit interconnection of the base unit 14 with one or more other components 62 that can be incorporated with the system 10 including, but not limited to, one or more other input devices, e.g., one or more desk top and/or lap top computers, an internet communication device and/or other computing device, remotely disposed relative to the oral care tool 12, and configured and programmed for generating game inputs and game control commands and for transmitting such inputs and commands to the base unit 14. In one embodiment, the internal communication module 41 of the base unit 14 can be configured and programmed to provide a wireless communication link 13' between the base unit 14 and one or more other components 62.

The one or more external communication ports 60 can also include ports configured to permit interconnection with the internet, and/or to provide a docketing station for receiving external memory cartridges, and/or to provide the ability to download external software.

As will be described below with reference to FIG. 5, many of the components of the base unit 14, and, in particular, the microcomputer system 50, the internal communication module 58, memory 56, the video display 18 and/or the speakers 20, can be configured and programmed to establish a wireless communication link 13' with at least a second oral care tool 12' to enable the base unit 14 to receive and to process game inputs and game control commands from the second oral tool 12', as well as sensor feedback outputs from sensors of the second oral tool 12', to configure the system 10 as a multi-user or multi-player system 10.

The base unit 14 includes, as mentioned, addressable memory or interchangeable memory 56 and optionally can be operatively coupled via one or more of the external communication ports 60 and/or the internal communication module 58 to an external and/or remote memory 65. Memory 56 of the base unit 14 incorporates electronic computer software for enabling one or more electronic and/or video games with the system 10. In addition, memory 56 can include preset, pre-programmed and/or programmable sets of instructions that cause the system 10 to implement and to enable oral care sessions, e.g., specific for a particular user 28 of the system 10 and/or specific to a particular oral care activity or function, as well as to cause the system 10 to implement and to enable prescribed oral care regimens comprising multiple oral care sessions, e.g., specific for a particular user 28 of the system 10 and specific for particular oral care activities or functions.

Memory 56 of the base unit 14, and/or external memory 65, are configured to record, compile and store sensor feedback provided by the sensors 34 and 36 of the one or more oral care tools 12 and 12', the efficacy ratings the microprocessor 41 and/or the microcomputer system 50 produce, and/or game data, such that, the base unit 14 can generate and display, or provide by other means, current, cumulative and/or historical files, records and reports of a user's brushing techniques and behaviors, efficacy ratings as well as the user's game performances and game goals achieved.

Figure 4:
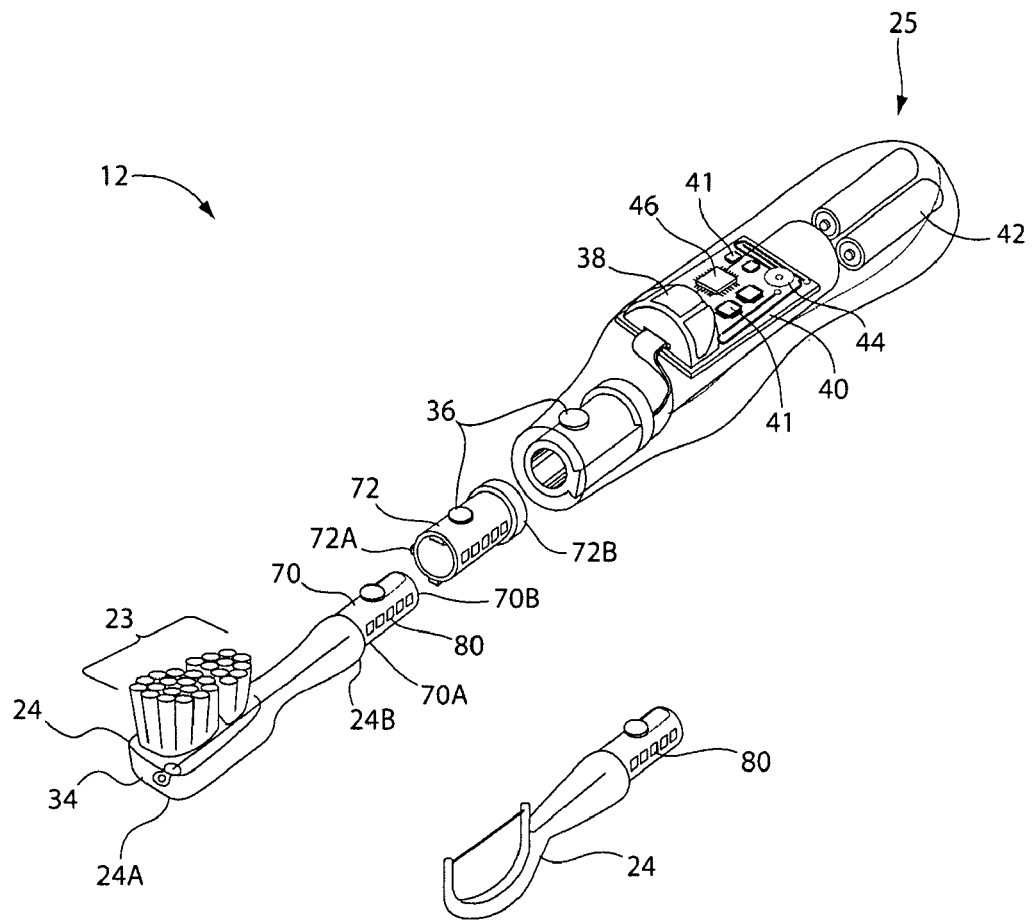
FIG. 4 is an exploded perspective view and a partial internal view of the oral care tool shown in FIGS. 1 and 2 configured as a toothbrush game enabler/controller.

Referring to FIG. 4, an exploded perspective and partial internal view of an exemplary oral care tool 12 is illustrated wherein the tool 12 is constructed and arranged as a toothbrush in accordance with the invention. The oral care tool 12 includes the brush head 24 configured with the plurality of bristles 13 at a distal end 24A of the brush head 24. The tool 12 further includes, as described above, the one or more sensors 36 contained within the interior of the handle 25, the one or more manual input switches 38, the PCB 40 operatively coupled to the microprocessor 46 and to the communication module 41, the one or more power sources 42 and the one or more speakers 44.

In the preferred embodiment, the brush head 24 is electrically powered and is constructed and arranged for tool-less and removable connection and detachment to the handle 25. In the preferred embodiment, the brush head 24 is removably connected and detached from the handle 25 via a quick-connection and lock 70 constructed and arranged at a proximal end 24B of the brush head 24 as a mechanical connection or an electro-mechanical coupling. The mechanical quick-connection and lock 70 can include any of a variety of mechanical connections including, but not limited to, a screw thread connection, a bayonet connection, a quarter-turn connection, a ball detent mechanism, a snap-lock connection and any other mechanical construction or configuration to provide quick and locking connection of the brush head 24 to a receiver 72, as will be described below, to thereby connect at least a portion of the brush head 24 to the handle 25. Alternatively, the quick-connection and lock 70 can be an electro-mechanical coupling that includes electrically-conductive connection points, e.g., disposed along or within its distal portion 70A and/or its proximal portion 70B, that are complementary to electrically-conductive connection points, e.g., disposed within the brush head 25, to help to support the conduction of electrical signals between the handle 25 and the brush head 25.

The tool 12 further includes the receiver 72 constructed and arranged to receive at least a portion of the proximal end 70B of the quick-connection and lock 70 and to receive at least a portion of a distal end 24 of the handle 25 to removably connect the brush head 24 with the handle 25. The receiver 72 can be constructed and arranged as an elastomeric receiver 72, e.g., constructed of one or more elastomeric or similar materials, to incorporate one or more sensors 36 with the receiver 72. As described above, such sensors 36 can include one or more strain gauges, load cells, force transducers, accelerometers, gravity sector sensors, gyroscopes and/or other motion or load sensing devices or sensors. The elastomeric receiver 72 enables forces applied to the oral care tool 12 to be translated to the sensors 36 for detection or measurement of, for instance, motions or loads of the tool 12.

Alternatively, or additionally, the receiver 72 can be an electromechanical coupling that includes electrically-conductive connection points, e.g., disposed along a distal portion 72A, that are complementary to the electrically-conductive connection points, e.g., disposed along the distal and/or proximal portions 70A and 70B of the quick-connection and lock 70, to help to support the conduction of electrical signals between the handle 25 and the brush head 25. The receiver 72 can also include electrically-conductive connection points, e.g., disposed along its proximal portion 72B, that are complementary to the electrically-conductive connection points, e.g., disposed along the distal end 24, of the handle 25 to help to support the conduction of electrical signals between the handle 25 and the brush head 24.

Further, as noted above, in the preferred embodiment, the brush head 24 is constructed and arranged as an encoded attachment 80 of the oral care tool 12 that provides identification or encoded signal(s) to the electronics of the handle 25, including the PCB 40 and the microprocessor 40, and/or to the electronics of the base unit 14, including the microcomputer system 50, such that the system 10 electronics in conjunction with programmed logic or software of the system 10 identify the individual brush head 24 to thereby identify the user associated with that particular brush head 24. In this manner, the system 10 is configured as a multi-user or multi-player system 10 that tracks use of individual brush heads 24 to track use of the system 10 by each individual user 28.

In addition, computer software of the system 10 can be programmed and/or can be programmable to incorporate and to recognize identification or encoded signal(s) of a brush head 24 for use as a password or software key that is recognizes by the system 10, e.g., the microcomputer 50 of the base unit 10, that causes the base unit 14 to run one or more electronic and/or video games in accordance with a set of rules of engagement and/or of play that are specific to the identification and encoded signal(s) that the system 10 identifies for a particular user 28. The system 10 can thereby provide electronic and/or video games that are individualized for specific users 28 of the system 10.

Software is a component in some or all of the embodiments of the system 10. In the preferred embodiment of the invention, software is stored in memory 56 of the base unit 14 and is designed for enabling a variety of electronic and/or video games. In addition, software is designed to enable oral care regimens, e.g., for oral maintenance or treatment, which are specific to each user 28 of the system 10 and/or, as will be described below with reference to FIG. 5A, are specific to each oral care activity the system 10 is configured to perform.

Electronic and/or video games of the system 10 are designed and programmed to provide entertainment and to motivate a user to practice proper oral care techniques and behaviors by encouraging and by reinforcing proper techniques and behaviors through feedback the system 10 provides to the user, while the user employs the oral care tool 12 to perform oral care activities and to play an electronic and/or video game of the base unit 14. Such feedback comprises, but is not limited to, enhanced or improved game play, game scoring and/or achievement of one or more game goals in response to the characteristics of the user's oral care techniques and behaviors that the system 10 senses and analyzes. In addition, the system 10 motivates a user to adhere to oral care regimens that the system 10 software enables, as will be described below.

In general, as the sensors 34 and 36 of the oral care tool 12 detect various oral care activities and/or characteristics of such activities, the sensor 34 and 36 outputs activate electronics of the base unit 14 to implement, initiate, play and/or display an electronic and/or video game in accordance with the system 10 software. For instance, in the preferred embodiment wherein the oral care tool 12 is configured as a toothbrush as described above, the temperature or thermal sensors 34 of the brush head 24 detect the presence of the brush head 24 in a user's mouth and thereby detect actual brushing occurring in the user's mouth with the oral care tool 12 as opposed to simulated tooth brushing with the oral care tool 12. The outputs of the temperature or thermal sensors 34 are analyzed by the microprocessor 46 of the tool 12 and/or the microcomputer system 50 of the base unit 14 to provide indications to the system 10 that tooth brushing is occurring in the user's mouth such that the system 10 software initiates, implements, plays and/or displays an electronic and/or video game. In addition, outputs from other sensors 36 are analyzed by the microprocessor 46 and/or the microcomputer system 50 to provide feedback to the system 10 representing characteristics of a user's oral care techniques and behaviors such that the system 10 software implements, initiates, plays and/or displays an electronic and/or video game. Further, game inputs and game control commands provided through actuation of the one or more input switches 30, 32 and 38 are received as inputs and are analyzed by the microprocessor 46 and/or the microcomputer system 50 to provide game inputs and commands to the system 10 such that the system 10 software implements, initiates, plays, and/or displays an electronic and/or video game. The system 10 software also implements, controls and/or modifies the content of an electronic and/or video game that the base unit 14 is running.

In addition, the microprocessor 46 and/or the microcomputer system 50 can, in accordance with the system 10 software, analyze and compute from the sensor 34 and 36 outputs efficacy ratings representing adequacy, appropriateness and/or sufficiency of a user's oral care techniques and behaviors. The system 10 software can employ a user's efficacy ratings, such as, for instance, temperature ratings (incidences of brushing in mouth), brushing duration ratings, brushing pressure ratings related to movement and direction of the tooth brush 12, and/or other ratings related to tooth brushing characteristics, alone or in any combination, to enhance or to improve the user's game play and, more particularly, the user's control of the game, game performance, scoring, game progress and achievement of game goals. In addition, during play of an electronic and/or video game, the system 10 software implements, controls and/or modifies the content of the game in response to such efficacy ratings. The system 10 thereby enables a user's game performance to serve as feedback that motivates and reinforces the user to continue with their oral care activity, e.g., for the duration of an oral care session as described below, and to modify or to improve their oral care techniques.

In the preferred embodiment, the outputs of the temperature or thermal sensors 34 are used by the system 10 software residing in the base unit 14 memory 56 to initiate, implement, play and/or display an electronic and/or video game. As mentioned above, the outputs of the temperature or thermal sensors 34 ensure tooth brushing is occurring in a user's mouth to avoid the user simply simulating tooth brushing to play a game. In addition, the system 10 software can be designed to employ the outputs of the temperature or thermal sensors 34 to implement an oral care session during which the base unit 14 runs an electronic and/or video game for a specific duration of time as long as a user employs the toothbrush 12 in their mouth for brushing their teeth.

The oral care sessions that the system 10 software enables can be preset or preprogrammed by the system 10 manufacturer(s) or by a physician, dentist, parent or other person, e.g., using the base unit 14 and its one or more manual input switches 30 and 32 and/or using another component 62, as described above, such as a desk top computer, a lap top computer or other computing device. In addition, or alternatively, the system 10 software can be programmable to create, modify and/or alter oral care sessions. For instance, the system 10 software can be preset or preprogrammed and/or can be programmable to permit a user to play an electronic and/or video game for a preferred number of oral care sessions per day, e.g., three sessions per day, with each session having a preferred duration, e.g., two minutes, to encourage continuous and regular tooth brushing. Brushing sessions can be scheduled over a specific period of time, e.g., over a 12 or 24 hour period, for a given user with enforced inactivity periods between sessions during which the base unit 14 for that user is disarmed to prevent tooth brushing between scheduled sessions. Scheduled brushing sessions and enforced inactivity periods thereby encourage the user to brush their teeth at regular intervals, such as after meals, and to prevent the user from initiating one brushing session after another simply to play a game.

In general, the system 10 software enables oral care sessions in accordance with sets of instructions stored in memory 56 of the base unit 14 that are programmable and/or are preset or preprogrammed as described above. Programming oral care sessions and inactivity periods in accordance with sets of instructions enables the system 10 to incorporate the oral care sessions into a prescribed oral care regimen that is specific for a user. The system 10 software implements and/or controls such regimens in accordance with the preset, preprogrammed and/or programmable sets of instructions stored in memory 56 to enable a prescribed oral care regimen for a specific user 28 of the system 10. In addition, as will be described below with reference to FIG. 5A, the system 10 software can enable a prescribed oral care regimen for a specific oral care activity whereby the system 10 software implements and/or controls, in accordance with preset, preprogrammed and/or programmable sets of instructions stored in memory 56, a prescribed oral care regimen for a specific care activity, including, but not limited to, tooth brushing, flossing, gum massaging and/or water-jetting teeth. Preset, preprogrammed and/or programmable oral care sessions and regimens help the system 10 to inhibit misuse of the system 10 and to encourage each user of the system 10 to adhere to prescribed oral care regimens.

In the context of tooth brushing, the outputs of the temperature or thermal sensors 34 are used by the system 10 software to detect whether a user has ceased brushing their teeth with the toothbrush 12 in their mouth before the expiration of a brushing session. For instance, if the temperature or thermal sensors 34 detect an interruption or cessation of brushing activity in a user's mouth during the brushing session and before the expiration of the preset, preprogrammed and/or programmable duration of the session, e.g., two minutes, the system 10 software will cause the base unit 14 to pause or stop the play of an electronic and/or video game, and to resume the game if the temperature or thermal sensors 34 detect the resumption of the brushing activity in the user's mouth within a defined interval of time, e.g., 3 or 5 seconds. If the sensors 34 detect an interruption or cessation of the tooth brushing in the user's mouth for a period longer than the defined interval, the system 10 software prohibits the base unit 14 from restarting the game until the next scheduled brushing session.

The outputs of the temperature or thermal sensors 34 can be coupled with the outputs of other sensors 34 and 36 of the toothbrush 12, such as, for instance, the outputs of one or more pressure transducers 34 and 36 and/or one or more accelerometers 34 and 36. As described above, one or more pressure transducers 34 and 36 can reside in the toothbrush 12 to detect the pressures the brush bristles 23 and the brush head 24 apply to a user's teeth when the user is brushing their teeth with the tooth brush 12 to thereby detect contact of the tooth brush 12 with surfaces of the user's teeth. The system 10 can analyze the outputs of the pressure transducers 34 and 36 alone as separate variables or in conjunction with the outputs of the temperature or thermal sensors 34 to produce efficacy ratings, as described above. Analyzing the pressure transducer 34 and 36 outputs, alone or in conjunction with the temperature or thermal sensor 34 outputs, can help the system 10 to determine whether tooth brushing is occurring in a user's mouth and to detect the cessation of tooth brushing, as well as to detect whether a user is applying the toothbrush 12 to most surfaces of their teeth to effect adequate tooth brushing as opposed to the user simply holding or placing the toothbrush 12 in their mouth and/or against one area of their teeth to play a game.

In addition, one or more accelerometers 34 and 36 can reside in the toothbrush 12 to detect the motions or movements of the brush head 24 and/or the toothbrush 12, to assess the direction and uniformity of the motions or movements, and/or to measure the accelerations of the brush head 24 and/or the toothbrush 12. The system 10 can analyze the outputs of the accelerometers 34 and 36 alone as separate variables or in conjunction with the outputs of the temperature or thermal sensors 324 to produce efficacy ratings, as described above. Analyzing the accelerometers 34 and 36 outputs, alone or in conjunction with the temperature or thermal sensors 34 outputs, can help the system 10 to determine whether tooth brushing is occurring in a user's mouth and to detect the cessation of tooth brushing, as well as to detect whether a user is moving the toothbrush 12 with sufficient speed over tooth surfaces and whether the user is applying the toothbrush 12 to most surfaces of their teeth to effect adequate tooth brushing as opposed to the user simply holding or placing the toothbrush in their mouth and/or against one area of their teeth to play a game.

In this manner, the system 10 can employ the outputs of the temperature or thermal sensors 34, alone or in conjunction with the outputs of the one or more pressure transducers 34 and 36 and/or the one or more accelerometers 34 and 36 to help the system 10 ensure a user is properly employing the tooth brush 12 to effect adequate tooth brushing.

Figure 5:
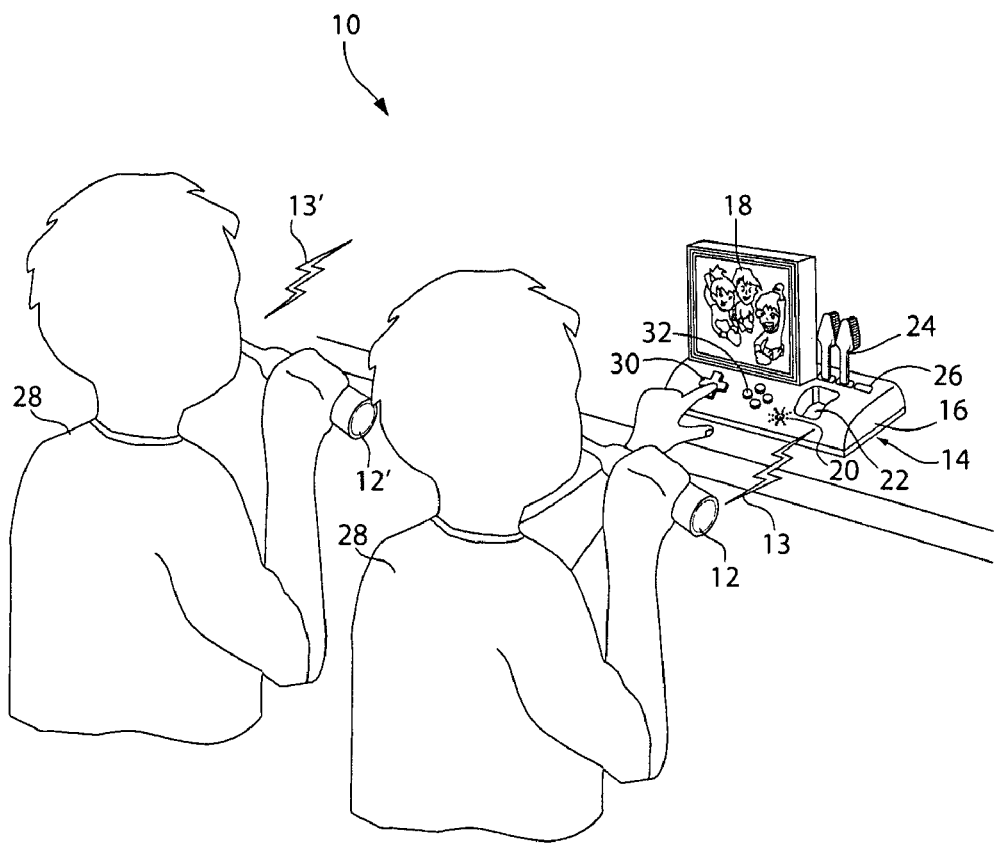
FIG. 5 is a schematic diagram of another embodiment of the oral care gaming system.
Figure 5A:
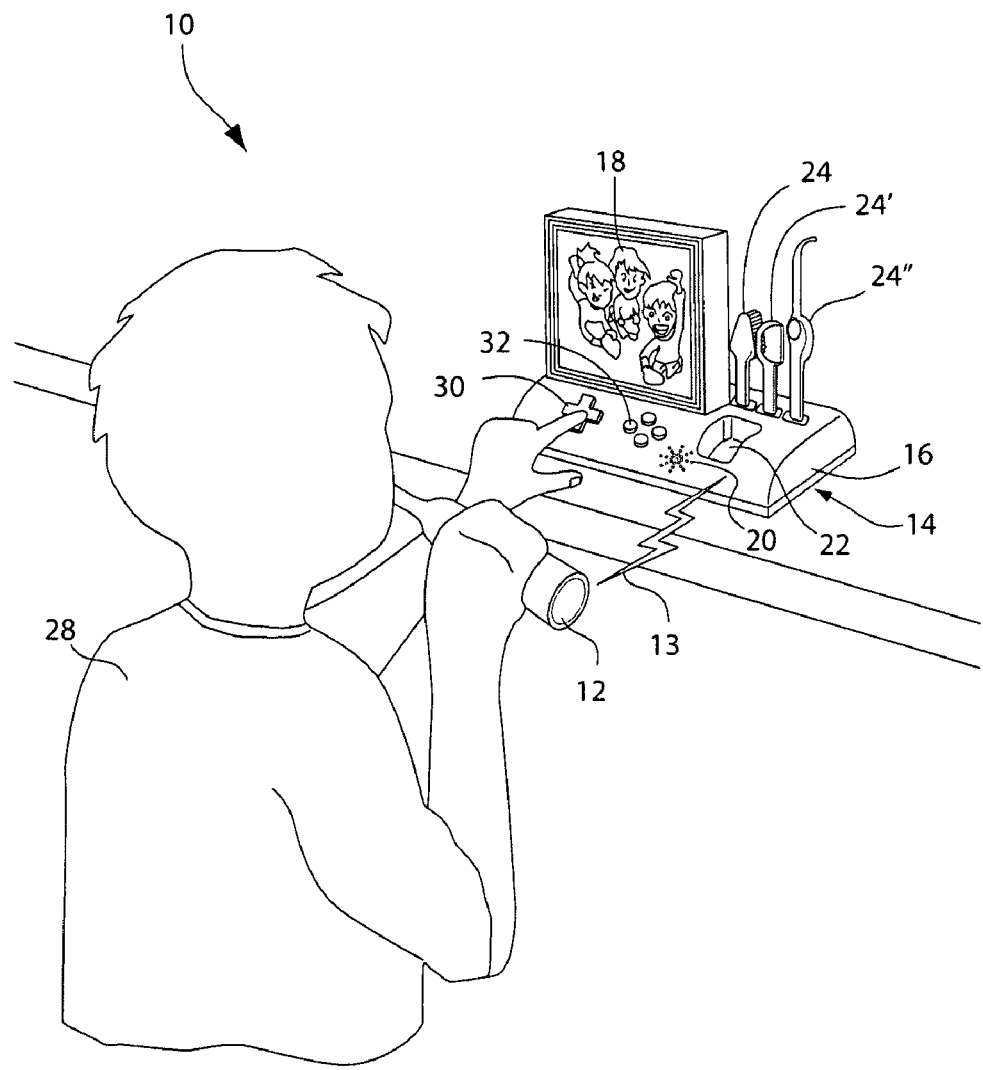
FIG. 5A is a schematic diagram of another embodiment of the oral care gaming system.

Referring to FIG. 5, in another aspect, the invention provides an oral care gaming system 10 including at least a second oral care tool 12' constructed and arranged for maintenance or treatment of the mouth, gums and/or teeth. The second oral care tool 12' is further designed and configured as a game enabler/controller, as described above with reference to FIGS. 1-4, to communicate with the base unit 14 and to interact with an electronic and/or video game of the base unit 14. The second oral care tool 12' permits the system 10 to be configured as a multi-user or multi-player system 10 wherein the system 10 enables each of two or more users of the system 10 to enable and to play the same or a different electronic and/or video game of the base unit 14, either alone or simultaneously with other users during the same oral care session, while the users are engaged in oral care activities using the oral care tools 12 and 12'.

Referring to FIG. 5A, and with further reference to FIGS. 1-4, in another aspect, the invention provides the system 10 designed and configured to perform multiple oral care functions whereby the system 10 and its users 28 can perform different oral care functions using the oral care tool 12. As described above, the oral care tool 12 is configured to receive and to removably connect to a multiple of different tool heads 24, 24', 24" with each tool head 24, 24', 24" configured for removable connection to the tool 12 to help to configure the system 10 as a multi-function system. Each tool head 24, 24', 24" is designed and is configured to perform one or more oral care functions and can include, but is not limited to, a tooth brush head 24, a flossing device head 24', a gum stimulating head 24", a water-jetting head and/or an implement configured as any combination thereof, to perform an oral care function, including, but not limited to, tooth brushing, flossing, gum massaging and/or water-jetting teeth.

As described above, each tool head 24, 24', 24" of the multi-function system 10 is programmed and/or is encoded 80 to identify a specific user 28 associated with the tool head 24, 24', 24" such that, when the tool head 24, 24', 24" is attached to the oral care tool 12, the base unit 14, e.g., the microcomputer 50, identifies the tool head 24, 24', 24", e.g., using identification or encoded signal(s) received from the tool head 24, 24', 24", to thereby identify the specific user 28 of the system 10. In addition, each tool head 24, 24', 24" of the multi-function system 10 is further programmed and/or is further encoded 80 to identify one or more specific functions of the tool head 24, 24', 24" such that, when the tool head 24, 24', 24" is attached to the oral care tool 12, the base unit 14, e.g., the microcomputer 50, identifies the oral care function(s) that the tool head 24, 24', 24" is to perform, e.g., using identification or signal(s) received from the tool head 24, 24', 24".

For instance, upon connection of the flossing tool head 24' to the oral care tool 12, the base unit 14, e.g., the microcomputer 50, identifies the specific user 28 and also identifies that an oral care function to be performed is flossing.

Recognition of a specific user 28 of the tool head 24, 24', 24" and oral care function(s) of the tool head 24, 24', 24" by the base unit 14 causes the system 10 software to enable oral care sessions that are preset or preprogrammed and/or are programmable in accordance with one or more sets of instructions stored in the base unit 14 memory 56. As described above, as the user 28 performs oral care activities with the oral care tool 12, the system 10 software causes the base unit 14 to enable one or more electronic and/or video games during an oral care session as long as the user 28 is properly employing the oral care tool 12. For instance, upon recognition of the tooth brush head 24 and a specific user 28 of that head 24, the system 10 software causes the base unit 14 to enable an electronic and/or video game during an oral care session for tooth brushing. Upon expiration of an oral care session for tooth brushing, the base unit 14 ceases enabling the game. Thereafter the user 28 may replace the tooth brush head 24 with another tool head, such as, for instance, the flossing head 24'. Upon recognition of the flossing head 24' and the specific user 28 by the base unit 14, the system 10 software causes the base unit 14 to enable the same or a different electronic and/or video game during a flossing session. Similarly, upon expiration of the flossing session, the user 28 can replace the flossing head 24' with the gum stimulating head 24' and the system 10 software similarly causes the base unit 14 to enable the same or a different electronic and/or video game to proceed during a gum massaging session as programmed for that particular user 28. The various oral care sessions that the system 10 software implements in response to the recognition of a tool head 24, 24', 24" and a specific user 28 of the oral care tool 12 enables the system 10 to implement an oral care regimen comprising different oral care sessions that are prescribed for that user 28. For instance, the set(s) of instructions may be programmed to prescribe a tooth brushing session to have a specific duration, e.g., two minutes, for a specific user 28 and may similarly prescribe a flossing session and/or a gum massaging session for that particular user 28 to each have a specific duration. In this manner, the system 10 permits the user 28 to play one or more electronic and/or video games over period of time, e.g., the total duration of specific oral care sessions, that is satisfactory to the user 28 and that allows or motivates the user 28 to practice each of the oral care functions of a prescribed oral care regimen.

Figure 6:
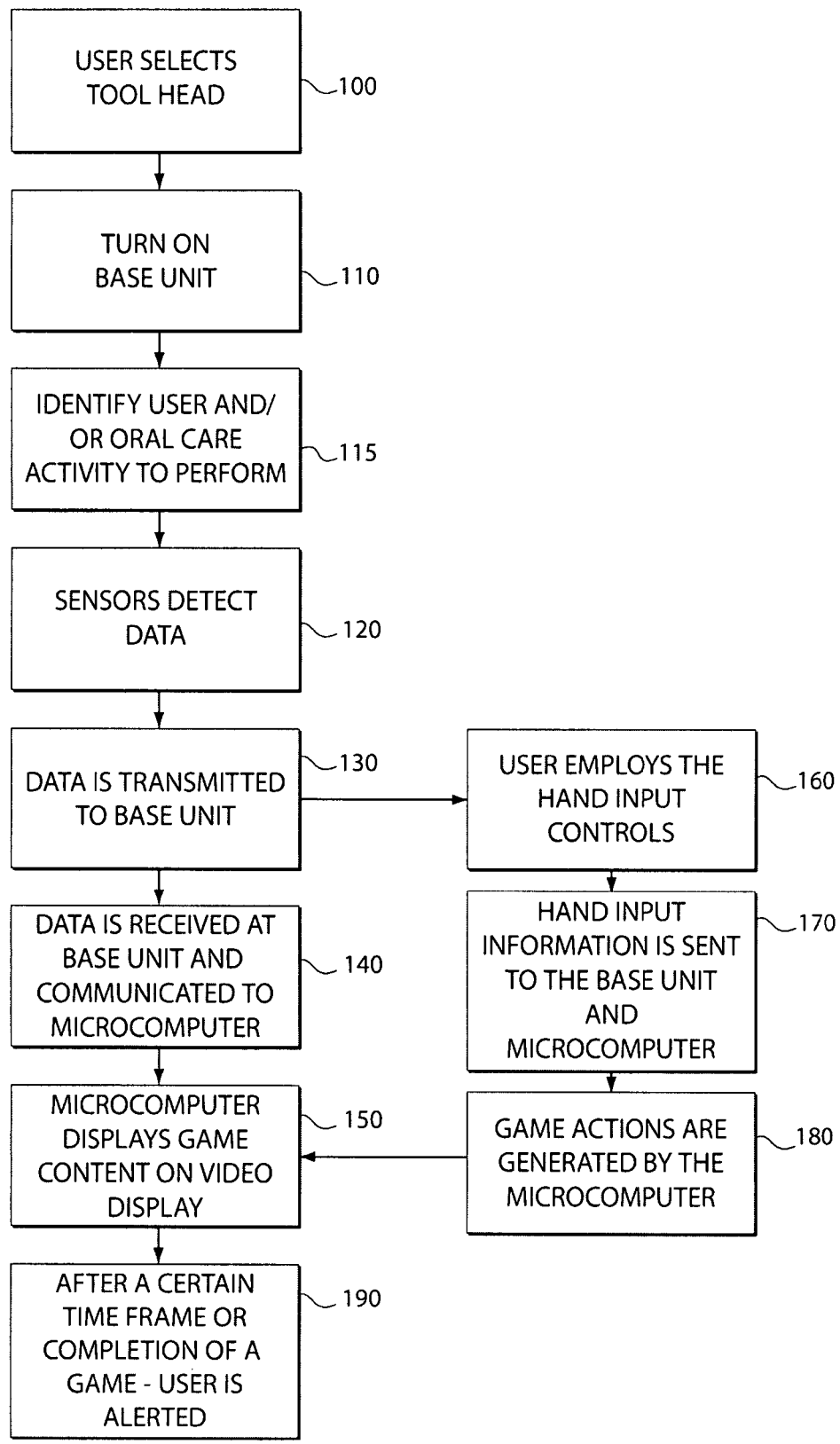
FIG. 6 is a block flow diagram illustrating a method of oral care gaming using the system shown in FIGS. 1, 5 and 5A.

Referring to FIG. 6, and with further reference to FIGS. 1-5, an exemplary process by which a user 28 interacts with the oral care gaming system 10 includes the stages shown. The process is exemplary only and not limiting, and may be modified, e.g., by adding, removing, and/or rearranging the stages shown.

At stage 100 a user 28 selects and attaches an oral care tool head 24 to the oral care tool 12. In the context of a multi-user system 10, the user 28 selects a tool head 24 that is designated or dedicated to that particular user 28. In the context of a multi-function system 10, the user 28 selects a tool head 24, 24', 24" that is designated or dedicated to that particular user 28 and that is appropriate for the oral care function or activity that the user 28 will perform.

At stage 110 the user 28 powers up or turns on the base unit 14 and selects an operating mode using one or more of the input switches 30 and 32. The user 28 turns on the oral care tool 12 using one or more of the input switches 38 along the handle 25 and/or the switches 30 and 32 on the base unit 14. A user 28 may load an electronic and/or video game into the base unit 14 using one or more of the external communication ports 60 to provide one or more new and/or additional games.

At stage 115, the base unit 14, e.g., the microcomputer 50, identifies the user 28 of the system 10, e.g., using identification or encoded signal(s) received from the programmed and/or encoded 80 tool head 24 in the context of the multi-user system 10, and further identifies the oral care function or activity to be performed by the system 10, e.g., using identification or enclosed signals(s) received from any one of different programmed and/or encoded 80 tool heads 24, 24', 24' of a multi-function system 10.

At stage 120 one or more types of sensors 34 and 36 in the oral care tool 12 detect oral care activities and, more particularly, characteristics of a user's oral care techniques and behaviors. In the preferred embodiment, one or more temperature or thermal sensors 34 detect temperatures in the user's mouth. In addition, the system 10 may include one or more pressure transducers 34 and 36, which detect the pressures the oral care tool 12 is applying to the user's teeth and/gums, and/or may include one or more accelerometers, which detect the direction and uniformity of the motions or movements and/or the accelerations of the oral care tool 12.

At stage 130 the outputs of the sensors 34 and 36 are transmitted as signals representing data to the base unit 14 through a hard-wired connection and/or a wireless communication link established between the tool 12 and the base unit 14.

At stage 140 the base unit 14 receives the signals and communicates with the microcomputer system 50.

At stage 150 the microcomputer system 50, in response to receipt of the signals, implements, initiates, plays and/or displays, via the video display 18, one or more electronic and/or video games residing in the base unit 14 memory 56 and/or downloaded by the user 28 from an external source through the communication port 60. On an ongoing basis, the microcomputer system 50 analyzes the signal data provided from the one or more of the sensors 34 and 36 to produce and to update oral care efficacy ratings of the user 28. The microcomputer system 50 employs one or more of the oral care efficacy ratings to create modified activities of the game being played and displayed based upon the one or more ratings. The oral care efficacy ratings are stored temporarily and/or permanently in memory 56 to provide current, cumulative and/or historical files and records of oral care efficacy ratings, signal data, oral care activities performed, and/or user game performances.

In some embodiments, at stage 160 the game ensues and the user 28 interacts with outputs the microcomputer system 50 produces to the video display 18 and uses the one or more input switches 38 to provide game inputs and game control commands to the base unit 14 to thereby interact with the displayed game content, and/or the user 28 uses the tool 12 via oral care activities, as detected, senses and/or measured by the one or more sensors 34 and 36, to interact with the displayed game content.

At stage 170 the game inputs and game control commands, and/or the oral care activities of the tool 12, are transmitted to the base unit 14.

At stage 180 the microcomputer system 50 acts upon the game inputs and game control commands and/or the oral care activities the tool 12 is performing to create selected responses and actions in the context of the electronic and/or video game the base unit 14 is running and displaying.

At stage 190 game play progresses until the time or real-time clock 54 counts a preset, preprogrammed and/or programmable value, e.g., that represents a duration of an oral care session, whereby the base unit 14 suspends the game play until the next oral care session.

Other embodiments are within the scope and spirit of the invention. For instance, the system 10 described with reference to FIG. 1, 5 or 5A can be configured and oriented to motivate users other than young children, such that, the base unit 14 enables one or more electronic and/or video games, e.g., a crossword puzzle, a word anagram or other word game, that is designed and configured for older children, adolescents and/or adults. In addition, the system 10 can be configured for and, in particular, the base unit 14 can include means to receive, data or information streaming from one or more sources via wireless, cable, satellite and/or internet communication in order to receive information and data oriented toward use of the system 10 by older children, adolescents and adults. For instance, the system 10 can be configured to receive, on an ongoing basis and/or intermittently, data or information streams related to any of a variety of phenomena, including, but not limited to, weather forecasts, stock performances, and publications of daily, weekly and monthly newspapers and magazines, whereby data or information are received, and optionally permanently or temporarily stored in memory 56, and displayed at the video display 18 of the base unit 14. In this context, a user's 28 employment of the oral care tool 12 for oral care activities and/or the sensor 34 and 36 outputs and/or the inputs provided to the system 10 via the input switches 30, 32 and 38, enable, activate, manipulate and/or modify the content of the data or information streams that are displayed at the video display 18. For instance, a user 28 can view a daily newspaper the system 10 receives via a data stream and displays at the video display 18, while the user 28 is employing the oral care tool 12, e.g., for tooth brushing. The sensor 34 and 36 outputs can maintain the display of the daily newspaper at the video display 18 while the outputs are continuously provided to the system 10, or, in other words, for the duration of the user 28 employing the oral care tool 12 for tooth brushing, e.g., as detected by the sensors 34 and 36. In addition, the user 28 can manipulate or modify the content displayed at the video display 18 by actuating any of the input switches 30, 32 and 38, such that, in the context of the displayed newspaper, the user 28 can turn pages of the newspaper, e.g., by activating a horizontal and/or a vertical scroll function of the video display 18.

In addition, the system 10 software can be configured to analyze, compile and/or store sensor 34 and 36 outputs, efficacy ratings the microprocessor 46 and/or the microcomputer system 50 produce, user game performance data and any other information related to the system 10 and/or a user's interaction with the system 10 to produce current, cumulative, and/or historical compilations, records and reports related to oral care activities and game performance. In addition, the system 10 can be further configured, as note above, for use in a display mode wherein current, cumulative and/or historical compilations, records and reports that the system 10 software analyzes, compiles and/or stores can be displayed at the video display 18. Further, the system 10 can download such current, cumulative, and/or historical compilations, records and reports, e.g., via one or more of the external communication ports 60.

In other instances, any current, cumulative and/or historical compilations, record and reports of game data or oral care data that the system 10 creates and maintains can be transmitted to the remote external memory 65, and/or can be transmitted, either through a hard-wired connection or more preferably through a wireless communication link 13', to one or more other components 62 incorporated with the system 10, e.g., a remote desk top or lap top computer, for display and/or storage of such data.

In another instance, the oral care tool 12 and the base unit 14 can be operatively connected via a hard-wired connection or linkage as an alternative to, or in addition to, the wireless communication link 13 and 13' established between the tool 12 and 12' and the base unit 14 via the internal communication modules 41 and 58. The hard-wired connection or linkage can be implemented with one or more cables between the tool 12 and 12' and the base unit 14 that are configured to conduct electrical signals between the tool 12 and 12' and the base unit 14. In addition, the one or more cables would include both signal lines to the base unit 14 and power lines from the base unit 14 to provide electrical power to the tool 12 and 12'. A hard-wired connection or linkage helps to reduce the processing electronics residing in the tool 12.

Having thus described at least one illustrative embodiment of the invention, various alterations, modifications and improvements will readily occur to those skilled in the art. Such alterations, modifications and improvements are intended to be within the scope and spirit of the invention. The invention can be implemented through microprocessors and/or microcomputer systems and associated software that instructs such computing devices to conduct various operations and functions. Due to the nature of software and such computing devices, one skilled in the art will readily recognize that the invention can be embodied in hardwiring hardware, firmware, and/or software or combinations of any of these. Accordingly, the foregoing description is by way of example only and is not intended as limiting. The invention's limit is defined only in the following claims and the equivalents thereto.

What is claimed is:

1. An oral care gaming system comprising:
   a) a first oral care tool configured for maintenance or treatment of a condition in a mouth or organs therein, the first oral care tool comprising:

one or more sensors for detecting temperatures of a user's mouth;
a speaker;
communication means for communicating with another component operatively coupled with the first oral care gaming system;
a removeable, reattachable head portion, wherein the head portion is encoded with identification data; and
b) an electronic gaming apparatus operatively coupled with the first oral care tool, the electronic gaming apparatus comprising:
communication means for communicating audio feedback of an electronic game to the first oral care tool;
a processor configured to receive the identification data; identify a user of the first oral care tool based upon the identification data; identify a type of the head portion based upon the identification data; configure the electronic game based upon both the user and the type of the head portion; and control the electronic game, wherein
the electronic game provides the audio feedback, and the audio feedback of the electronic game is responsive to inputs received from the one or more sensors for detecting temperatures.

2. The system of claim 1, wherein the communication means of the first oral care tool and the communication means of the electronic gaming apparatus includes one or more electrical conductors that operatively couple the first oral care tool to the electronic gaming apparatus.

3. The system of claim 1, wherein at least one of the communication means of the first oral care tool and the communication means of the electronic gaming apparatus includes a wireless transmission system configured to establish a wireless communication link between the first oral care tool and the electronic gaming apparatus.

4. The system of claim 1, wherein the electronic gaming apparatus further includes memory operatively coupled with the processor and storing at least one set of instructions for implementing at least one regimen of oral care maintenance or treatment.

5. The system of claim 4, wherein the audio feedback of the electronic game is implemented in accordance with the at least one set of instructions.

6. The system of claim 1, wherein the electronic gaming apparatus further includes at least one external communication port for interconnection with at least one input device disposed remotely relative to the electronic gaming apparatus or the first oral care tool.

7. The system of claim 6, wherein the at least one input device includes at least one of a computer, a computing device and an internet communication device configured to provide inputs to the processor.

8. The system of claim 6, wherein the electronic gaming apparatus further includes means to establish a wireless communications link between the electronic gaming apparatus and the at least one input device disposed remotely relative to the electronic gaming apparatus or the first oral care tool.

9. The system of claim 1, further comprising a timer to determine a duration of use of the first oral care tool for an oral care session.

10. The system of claim 9, wherein the audio feedback of the electronic game ceases upon the processor receiving inputs from the one or more sensors for detecting temperatures, the inputs indicating a cessation of use of the first oral care tool before an expiration of the oral care session.

11. The system of claim 10, wherein the audio feedback of the electronic game resumes upon the processor receiving inputs from the one or more sensors for detecting temperatures, inputs indicating a resumption of use of the first oral care tool before the expiration of a given interval of time.

12. The system of claim 1, wherein the another component operatively coupled with the oral care gaming system includes at least the electronic gaming apparatus.

13. The system of claim 1, further comprising at least a second oral care tool configured for maintenance or treatment of a condition in the mouth or organs therein, the second oral care tool comprising one or more sensors for detecting temperatures of the user's mouth, and communication means for communicating with the another component operatively coupled with the oral care gaming system, wherein the another component includes at least the electronic gaming apparatus.

14. The system of claim 13, wherein the inputs received from the one or more sensors for detecting temperatures of the first and the second oral care tools are coupled onto the audio feedback of the electronic game.

15. The system of claim 13, wherein inputs received from the one or more sensors for detecting temperatures of the second oral care tool are coupled onto the audio feedback of a second electronic game.

16. The system of claim 13, wherein the first and the second oral care tools each include a device selected from a group consisting of a tooth brush, a flossing device, a gum stimulating instrument, a water jet device, an implement configured as any combination thereof, and any combination thereof.

17. The system of claim 1, wherein the first oral care tool includes a device selected from a group consisting of a tooth brush, a flossing device, a gum stimulating instrument, a water-jet device, an implement configured as any combination thereof, and any combination thereof.

18. The system of claim 1, wherein the first oral care tool further comprises one or more sensors for detecting pressures which the first oral care tool applies to at least one of the user's mouth and teeth in the user's mouth, and wherein the audio feedback of the electronic game being responsive to one or more inputs received from the one or more sensors for detecting pressures.

19. The system of claim 1, wherein the first oral care tool further comprises one or more sensors for detecting at least one of movement, direction and acceleration of the first oral care tool within the user's mouth and along teeth in the user's mouth, and wherein the audio feedback of the electronic game being responsive to inputs received from the one or more sensors for detecting at least one of movement, direction or acceleration.

20. The system of claim 1, wherein the electronic gaming apparatus further comprises a video display for displaying images of the electronic game.

* * * * *

UNITED STATES PATENT AND TRADEMARK OFFICE
CERTIFICATE OF CORRECTION

Page 1 of 1

PATENT NO. : 7,976,388 B2
APPLICATION NO. : 11/728259
DATED : July 12, 2011
INVENTOR(S) : Sung K. Park and Douglas C. Dayton It is certified that error appears in the above-identified patent and that said Letters Patent is hereby corrected as shown below:

Column 21, Line 5, "component operatively coupled with the first oral care" should read
-- component operatively coupled with the oral care --

Signed and Sealed this
Eighteenth Day of October, 2011

David J. Kappos
*Director of the United States Patent and Trademark Office*